(12) United States Patent
Sniadecki et al.

(10) Patent No.: US 10,006,900 B2
(45) Date of Patent: *Jun. 26, 2018

(54) DEVICES TO EXPOSE CELLS TO FLUID SHEAR FORCES AND ASSOCIATED SYSTEMS AND METHODS

(71) Applicant: University of Washington, Seattle, WA (US)

(72) Inventors: Nathan J. Sniadecki, Seattle, WA (US); Lucas Ting, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/832,164

(22) Filed: Aug. 21, 2015

(65) Prior Publication Data

US 2016/0024454 A1    Jan. 28, 2016

Related U.S. Application Data

(62) Division of application No. 13/663,339, filed on Oct. 29, 2012, now Pat. No. 9,140,684.

(Continued)

(51) Int. Cl.
    *C12M 1/42*     (2006.01)
    *G01N 33/49*    (2006.01)
    (Continued)

(52) U.S. Cl.
    CPC ......... *G01N 33/4905* (2013.01); *C12M 23/20* (2013.01); *C12M 23/26* (2013.01);
    (Continued)

(58) Field of Classification Search
    None
    See application file for complete search history.

(56) References Cited

U.S. PATENT DOCUMENTS

| 4,986,964 | A | 1/1991 | Carr et al. |
| 5,205,159 | A | 4/1993 | Carr, Jr. |

(Continued)

FOREIGN PATENT DOCUMENTS

| CN | 101874208 A | 10/2010 |
| CN | 102150042 A | 8/2011 |

(Continued)

OTHER PUBLICATIONS

Couzon et al "Critical stresses for cancer cell detachment in microchannels" Eur Biophys J, 2009, 38: 1035-1047.*

(Continued)

*Primary Examiner* — Betty J Forman
(74) *Attorney, Agent, or Firm* — Perkins Coie LLP (57) ABSTRACT

The present technology relates generally to devices to expose cells to fluid shear forces and associated systems and methods. In particular, several embodiments are directed toward devices to expose cells to fluid shear forces in order to measure changes in internal cell forces. In some embodiments, a fluidic device includes a flow unit configured to induce fluid flow through the device. The device further includes a fluid channel configured to accept a biological sample dispersed on an array of flexible structures. The flow unit can be configured to induce disturbed and/or laminar flow in the fluid channel. The device can further include optical or magnetic detection means configured to measure a degree of deflection of one or more flexible structures in the array.

15 Claims, 5 Drawing Sheets

Related U.S. Application Data (60) Provisional application No. 61/552,052, filed on Oct. 27, 2011, provisional application No. 61/645,191, filed on May 10, 2012, provisional application No. 61/709,809, filed on Oct. 4, 2012.

(51) Int. Cl.
    *G01N 33/53* (2006.01)
    *C12M 1/34* (2006.01)
    *G01N 15/14* (2006.01)
    *G01N 15/10* (2006.01)
    *C12M 1/00* (2006.01)
    *B01L 3/00* (2006.01)

(52) U.S. Cl.
CPC ............ *C12M 29/00* (2013.01); *C12M 35/04* (2013.01); *C12M 41/46* (2013.01); *G01N 15/1056* (2013.01); *G01N 15/1459* (2013.01); *G01N 15/1463* (2013.01); *G01N 33/5302* (2013.01); *B01L 3/502746* (2013.01); *G01N 15/1404* (2013.01); *G01N 2015/1006* (2013.01)

(56) References Cited

U.S. PATENT DOCUMENTS

| | | |
|---|---|---|
| 6,573,104 B2 | 6/2003 | Carr et al. |
| 7,163,659 B2 | 1/2007 | Stasiak et al. |
| 7,192,726 B1 | 3/2007 | Carr et al. |
| 7,670,831 B2 | 3/2010 | Lee et al. |
| 7,774,951 B2 | 8/2010 | Hartmann et al. |
| 8,187,865 B2 | 5/2012 | Yun et al. |
| 8,278,919 B2 | 10/2012 | Fischer et al. |
| 8,425,840 B2 | 4/2013 | Hosokawa et al. |
| 9,140,684 B2 | 9/2015 | Sniadecki et al. |
| 2002/0172963 A1 | 11/2002 | Kelley et al. |
| 2002/0187504 A1 | 12/2002 | Reich et al. |
| 2003/0044853 A1 | 3/2003 | Socks et al. |
| 2003/0092016 A1 | 5/2003 | Wiggins et al. |
| 2003/0097120 A1 | 5/2003 | Santerre |
| 2003/0154771 A1 | 8/2003 | De Charmoy Grey et al. |
| 2003/0215816 A1 | 11/2003 | Sundararajan et al. |
| 2004/0151629 A1 | 8/2004 | Pease et al. |
| 2005/0015001 A1 | 1/2005 | Kresh et al. |
| 2005/0019791 A1 | 1/2005 | Jung et al. |
| 2006/0063153 A1 | 3/2006 | Mamine et al. |
| 2006/0121502 A1 | 6/2006 | Cain et al. |
| 2007/0116607 A1 | 5/2007 | Wang et al. |
| 2007/0194658 A1 | 8/2007 | Zhang et al. |
| 2007/0235340 A1 | 10/2007 | Naughton |
| 2008/0026476 A1 | 1/2008 | Howell et al. |
| 2008/0160548 A1 | 7/2008 | Klapproth |
| 2008/0234236 A1 | 9/2008 | Veltri et al. |
| 2008/0261261 A1 | 10/2008 | Grimes et al. |
| 2009/0045063 A1 | 2/2009 | Kang et al. |
| 2009/0130744 A1 | 5/2009 | Saldivar et al. |
| 2009/0181421 A1 | 7/2009 | Kapur et al. |
| 2010/0006439 A1 | 1/2010 | Ham et al. |
| 2010/0324838 A1 | 12/2010 | Hartmann et al. |
| 2011/0151500 A1 | 6/2011 | Hosokawa et al. |
| 2011/0189719 A1 | 8/2011 | Kuo et al. |
| 2011/0203367 A1 | 8/2011 | Huang et al. |
| 2012/0015368 A1 | 1/2012 | Del Galdo et al. |
| 2012/0058500 A1 | 3/2012 | Mitchell et al. |
| 2012/0071342 A1 | 3/2012 | Lochhead et al. |
| 2012/0142556 A1 | 6/2012 | Parker et al. |
| 2012/0156791 A1 | 6/2012 | Superfine et al. |
| 2012/0161207 A1 | 6/2012 | Homyk et al. |
| 2012/0212732 A1 | 8/2012 | Santori et al. |
| 2013/0109012 A1 | 5/2013 | Sniadecki et al. |
| 2013/0237453 A1 | 9/2013 | Chander |
| 2015/0015001 A1 | 1/2015 | Fabbro |
| 2015/0056643 A1 | 2/2015 | Bielawski et al. |
| 2016/0061814 A1 | 3/2016 | Sniadecki |
| 2016/0363600 A1 | 12/2016 | Sniadecki |

FOREIGN PATENT DOCUMENTS

| | | |
|---|---|---|
| CN | 104428671 A | 3/2015 |
| EP | 2053387 A1 | 4/2009 |
| EP | 2208531 | 7/2010 |
| EP | 2208531 A1 | 7/2010 |
| JP | 2002543403 A | 12/2002 |
| JP | 2005517159 A | 6/2005 |
| JP | 2005526512 A | 9/2005 |
| JP | 2005308484 A | 11/2005 |
| JP | 2006505795 A | 2/2006 |
| JP | 2006517024 A | 7/2006 |
| JP | 2009068874 A | 4/2009 |
| JP | 2012531595 A | 12/2012 |
| WO | 2002090976 | 11/2002 |
| WO | 2004062570 | 7/2004 |
| WO | 2004093641 A2 | 11/2004 |
| WO | 2006055318 | 5/2006 |
| WO | 2006055318 A2 | 5/2006 |
| WO | 2006084242 | 8/2006 |
| WO | 2008103430 | 8/2008 |
| WO | 2010151780 | 12/2010 |
| WO | 2012048288 | 4/2012 |
| WO | 2012048288 A1 | 4/2012 |
| WO | 2012048269 A8 | 2/2013 |
| WO | 2013076157 | 5/2013 |
| WO | 2013076157 A1 | 5/2013 |
| WO | 2013169379 A1 | 11/2013 |
| WO | 2014210388 A1 | 12/2014 |

OTHER PUBLICATIONS

Office Action dated Oct. 26, 2015 in Chinese Patent Application No. 201380036951.8, 19 pages.

Feghhi et al., "Mechanobiology of Platelets: Techniques to Study the Role of Fluid Flow and Platelet Retraction Forces at the Micro- and Nano-Scale," Intl. J. Mol. Sci., vol. 12, No. 12: pp. 9009-9030. (Dec. 7, 2011).

Conant et al., "Well Plate Microfluidic System for Investigation of Dynamic Platelet Behavior Under Variable Shear Loads," Biotech. Bioeng., vol. 108, No. 12: pp. 2978-2987 (Jul. 16, 2011).

Gutierrez et al., "Microfluidic Devices for Studies of Shear-Dependent Platelet Adhesion," Lab on a Chip, vol. 8, No. 9, (Jan. 1, 2008).

Haenecke et al. (2007) Thrombelastography today: Practicability and analytical power. Transfusion Medicine and Hemotherapy. 34(6): p. 421-428.

Harris et al. (2000) The leukocyte integrins. J Biol Chem. 275(31): p. 23409-12.

Hartman et al. (2009) Cluster size regulates protein sorting in the immunological synapse. Proc Natl Acad Sci U S A. 106(31): p. 12729-34.

http://www.who.int/entity/healthinfo/global_burden_disease/gbd-deathdalycountryestimates.2004.xls, World Health Org., Department Measurement and Health Information; Feb. 2009.

Inoue et al (2008) Redundant mechanism of platelet adhesion to laminin and collagen under flow: involvement of von Willebrand factor and glycoprotein Ib-IX-V. J Biol Chem. 283(24): p. 16279-82.

Inoue et al. (2006) Laminin stimulates spreading of platelets through integrin alpha6beta1-dependent activation of GPVI. Blood. 107(4): p. 1405-12.

Jackson et al. (2009) Dynamics of platelet thrombus formation. J Thromb Haemost. 7 Suppl 1: p. 17-20.

Jackson, SP (2011) Arterial thrombosis—insidious, unpredictable and deadly. Nat Med 17(11):1423-1436.

Jacoby et al. Platelet activation and function after trauma. J Trauma 51, 639-647, (2001).

Jiang et al. Ultralow-fouling, functionalizable, and hydrolyzable zwitterionic materials and their derivatives for biological applications. Adv Mater 22, 920-932, (2010).

(56) References Cited

OTHER PUBLICATIONS

Kantak et al., "Microfluidic Platelet Function Analyzer for Shear-Induced Platelet Activation Studies," 2nd Annual International IEEE-EMBS Special Topic Conference on Microtechnologies in Medicine & Biology, pp. 169-173 (May 2-4, 2002).
Kashuk et al. (2010) Postinjury coagulopathy management: goal directed resuscitation via POC thrombelastography. Ann Surg. 251(4): p. 604-14.
Kashuk et al. The emerging role of rapid thromboelastography in trauma care. J Trauma 67, 417-418, (2009).
Kasirer-Friede et al. (2002) Lateral clustering of platelet GP Ib-IX complexes leads to up-regulation of the adhesive function of integrin alpha IIbbeta 3. J Biol Chem 277(14):11949-11956.
Kasirer-Friede et al. (2004) Signaling through GP Ib-IX-V activates alpha IIb beta 3 independently of other receptors. Blood 103(9):3403-3411.
Katori et al. (2005) The effects of platelet count on clot retraction and tissue plasminogen activator-induced fibrinolysis on thrombelastography. Anesth Analg. 100(6): p. 1781-5.
Kaufmann et al. (1997) Usefulness of thrombelastography in assessment of trauma patient coagulation. J Trauma. 42(4): p. 716-20; discussion 720-2.
Kaunas et al. Cooperative effects of Rho and mechanical stretch on stress fiber organization. Proc Natl Acad Sci U S A 102: 15895-15900, 2005.
Kelly et al. (2008) Injury severity and causes of death from Operation Iraqi Freedom and Operation Enduring Freedom: 2003-2004 versus 2006. J Trauma. 64(2 Suppl): p. S21-6; discussion S26-7.
Kroll et al. (1991) von Willebrand factor binding to platelet GpIb initiates signals for platelet activation. J Clin Invest 88(5):1568-1573.
Lam et al. (2011) Mechanics and contraction dynamics of single platelets and implications for clot stiffening. Nature materials 10(1):61-66.
Langille BL. Morphologic responses of endothelium to shear stress: reorganization of the adherens junction. Microcirculation 8: 195-206, 2001.
Le Duc et al. Vinculin potentiates E-cadherin mechanosensing and is recruited to actin-anchored sites within adherens junctions in a myosin II-dependent manner. J Cell Biol 189: 1107-1115, 2010.
Lemmon et al. (2005) Shear force at the cell-matrix interface: enhanced analysis for microfabricated post array detectors. Mech Chem Biosyst. 2(1): p. 1-16.
Leng et al. (1998) RhoA and the function of platelet integrin alphaIIbbeta3. Blood. 91(11): p. 4206-15.
Leon et al. (2007) Megakaryocyte-restricted MYH9 inactivation dramatically affects hemostasis while preserving platelet aggregation and secretion. Blood. 110(9): p. 3183-91.
Leon, C. et al. Megakaryocyte-restricted MYH9 inactivation dramatically affects hemostasis while preserving platelet aggregation and secretion. Blood 110, 3183-3191, (2007).
Levrat et al. (2008) Evaluation of rotation thrombelastography for the diagnosis of hyperfibrinolysis in trauma patients. Br J Anaesth. 100(6): p. 792-7.
Li et al. (2003). Detection of single micron-sized magnetic bead and magnetic nanoparticles using spin valve sensors for biological applications. Journal of Applied Physics 93(10): 7557-7559.
Liang et al. "Platelet Retraction Force Measurements Using Flexible Post Force Sensors." Lab Chip, vol. 10, No. 8, pp. 991-998 (Jan. 1, 2010).
Liu et al. (2010) Mechanical Forces in Endothelial Cells During Firm Adhesion and Early Transmigration of Human Monocytes. Cellular and Molecular Bioengineering. 3(1): p. 50-59.
Liu et al. Mechanical tugging force regulates the size of cell-cell junctions. Proc Natl Acad Sci U S A 107: 9944-9949, 2010.
Maani et al. (2009) Coagulopathy in traumapatients: what are the main influence factors? Current Opinion in Anesthesiology. 22(2): p. 255-260.

Maeda et al. (2005) Increased tyrosine phosphorylation of platelet proteins including pp125(FAK) suggests endogenous activation and aggregation in pulmonary hypertension. Clin Appl Thromb Hemost. 11(4): p. 411-5.
Mailhac et al. (1994) Effect of an eccentric severe stenosis on fibrin(ogen) deposition on severely damaged vessel wall in arterial thrombosis. Relative contribution of fibrin(ogen) and platelets. Circulation 90(2):988-996.
Martini et al. Thrombelastography is better than PT, aPTT, and activated clotting time in detecting clinically relevant clotting abnormalities after hypothermia, hemorrhagic shock and resuscitation in pigs. J Trauma 65, 535-543, (2008).
Martins et al. (2010). Challenges and trends in the development of a magnetoresistive biochip portable platform. Journal of Magnetism and Magnetic Materials 322(9-12): 1655-1663.
Maruthamuthu et al. Cell-ECM traction force modulates endogenous tension at cell-cell contacts. Proc Natl Acad Sci U S A 108: 4708-4713, 2011.
Mazzucato et al. (2002) Sequential cytoplasmic calcium signals in a 2-stage platelet activation process induced by the glycoprotein Ibalpha mechanoreceptor. Blood 100(8):2793-2800.
Mehta et al. Signaling mechanisms regulating endothelial permeability. Physiol Rev 86: 279-367, 2006.
Miao et al. Effects of flow patterns on the localization and expression of VE-cadherin at vascular endothelial cell junctions: in vivo and in vitro investigations. J Vasc Res 42: 77-89, 2005.
Moore et al. (2010) Stretchy proteins on stretchy substrates: the important elements of integrin-mediated rigidity sensing. Dev Cell. 19(2): p. 194-206.
Morii et al. (1992) A rho gene product in human blood platelets. II. Effects of the ADP-ribosylation by botulinum C3 ADP-ribosyltransferase on platelet aggregation. J Biol Chem. 267(29): p. 20921-6.
Mrksich, M. (2009) Using self-assembled monolayers to model the extracellular matrix. Acta Biomater. 5(3): p. 832-41.
Nance M. (ed), National Trauma Data Bank Annual Report 2011.
Nelson et al. (2003) Degradation of micropatterned surfaces by cell-dependent and -independent processes. Langmuir. 19(5): p. 1493-1499.
Nelson et al. (2005) Emergent patterns of growth controlled by multicellular fom1 and mechanics. Proc Natl Acad Sci U S A. 102(33): p. 11594-11599.
Nesbitt et al. (2009) A shear gradient-dependent platelet aggregation mechanism drives thrombus formation. Nat Med. 15(6): p. 665-73.
Ni et al. (2003) Plasma fibronectin promotes thrombus growth and stability in injured arterioles. Proc Natl Acad Sci U S A. 100(5): p. 2415-9.
Nieswandt et al. (2003) Platelet-collagen interaction: is GPVI the central receptor? Blood 102(2):449-461.
Niles et al. Increased mortality associated with the early coagulopathy of trauma in combat casualties. J Trauma 64, 1459-1463; discussion 1463-1455, (2008).
Noria et al. Transient and steady-state effects of shear stress on endothelial cell adherens junctions. Circ Res 85: 504-514, 1999.
Okorie et al. (2006) Matrix protein microarrays for spatially and compositionally controlled microspot thrombosis under laminar flow. Biophys J. 91(9): p. 3474-81.
Ono et al. (2008) Identification of a fibrin-independent platelet contractile mechanism regulating primary hemostasis and thrombus growth. Blood. 112(1): p. 90-99.
Phelps et al. Spatial variations in endothelial barrier function in disturbed flows in vitro. Am J Physiol Heart Circ Physiol 278: H469-476, 2000.
Plotkin et al. (2008) A reduction in clot formation rate and strength assessed by thrombelastography is indicative of transfusion requirements in patients with penetrating injuries. J Trauma. 64(2 Suppl): p. S64-8.
Pokutta et al. Structure and mechanism of cadherins and catenins in cell-cell contacts. Annu Rev Cell Dev Biol23: 237-261, 2007.
Potard et al. Cytoskeletal mechanics in confluent epithelial cells probed through integrins and E-cadherins. Am J Physiol 272: C1654-1663, 1997.

(56) References Cited

OTHER PUBLICATIONS

Reininger AJ, et al. (2006) Mechanism of platelet adhesion to von Willebrand factor and microparticle formation under high shear stress. Blood 107(9):3537-3545.
Reininger, A.J., Function of von Willebrand factor in haemostasis and thrombosis. Haemophilia, 2008. 14 Suppl 5: p. 11-26.
Rossaint et al.(2010) Management of bleeding following major trauma: an updated European guideline. Critical Care. 14(2): p. 1-29.
Rugeri et al. (2007) Diagnosis of early coagulation abnormalities in trauma patients by rotation thrombelastography. J Thromb Haemost. 5(2): p. 289-95.
Ruggeri et al. (2006) Activation—independent platelet adhesion and aggregation under elevated shear stress. Blood. 108(6): p. 1903-10.
Ruggeri, Z.M. (2009) Platelet adhesion under flow. Microcirculation. 16(1): p. 58-83.
Sanchez-Cortes et al.(2009) The platelet integrin alphaIIbbeta3 binds to the RGD and AGD motifs in fibrinogen. Chem Biol. 16(9): p. 990-1000.
Savage et al (1998) Specific synergy of multiple substrate-receptor interactions in platelet thrombus formation under flow. Cell. 94(5): p. 657-66.
Savage et al. (1992) Modulation of platelet function through adhesion receptors. A dual role for glycoprotein IIb-IIIa (integrin alpha IIb beta 3) mediated by fibrinogen and glycoprotein Ib-von Willebrand factor. J Biol Chem. 267(16): p. 11300-6.
Savage et al. (1996) Initiation of platelet adhesion by arrest onto fibrinogen or translocation on von Willebrand factor. Cell 84(2):289-297.
Savage et al. (2002) Functional self-association of von Willebrand factor during platelet adhesion under flow. Proc Natl Acad Sci U S A. 99(1): p. 425-30.
Schmitt et al. Trauma in Washington State, A Chart Report of the First 15 Years 1995-2009. DOH 689-001, Feb. 2011.
Schochl et al. Goal-directed coagulation management of major trauma patients using thromboelastometry (ROTEM)-guided administration of fibrinogen concentrate and prothrombin complex concentrate. Grit Care 14, R55, (2010).
Schoenwaelder et al. (2002) RhoA sustains integrin alpha IIbbeta 3 adhesion contacts under high shear. J Biol Chem. 277(17): p. 14738-46.
Seattle & King County Division of Emergency Medical Services: 2012 Annual Report.
Shankaran et al. (2003) Aspects of hydrodynamic shear regulating shear-induced platelet activation and self-association of von Willebrand factor in suspension. Blood 101(7):2637-2645.
Shattil et al. (1998) Integrin signaling: the platelet paradigm. Blood. 91(8): p. 2645-57.
Shattil et al. (2010) The final steps of integrin activation: the end game. Nat Rev Mol Cell Biol 11(4):288-300.
Shay-Salit et al. VEGF receptor 2 and the adherens junction as a mechanical transducer in vascular endothelial cells. Proc Natl Acad Sci US A 99: 9462-9467, 2002.
Shinjo, T., Nanomagnetism and Spintronics. (2009), Elsevier B.V. Boston.
Shiu et al. Rho mediates the shear-enhancement of endothelial cell migration and traction force generation. Biophys J 86: 2558-2565, 2004.
Siedlecki et al. Shear-dependent changes in the three-dimensional structure of human von Willebrand factor. Blood, 1996. 88(8): p. 2939-50.
Simmons et al. (1969) Coagulation disorders in combat casualties. I. Acute changes after wounding. II. Effects of massive transfusion. 3. Post-resuscitative changes. Ann Surg. 169(4): p. 455-82.
Sniadecki et al. (2007) Microfabricated silicone elastomeric post arrays for measuring traction forces of adherent cells. Methods Cell Biol. 83: p. 313-28.
Sniadecki et al. (2001) A Silicon Microfluidic Multiplexer Using Field Effect Flow Control. in Micro Total Analysis Systems 2001. Monterey, California: Kluwer, 1 pg.
Sniadecki et al. (2004) Induced pressure pumping in polymer microchannels via field-effect flow control. Anal Chem. 76(7): p. 1942-7.
Sniadecki et al., "Magnetic Microposts as an Approach to Apply Forces to Living Cells." Proc. Natl. Acad. Sci.U.S.A., vol. 104, No. 34, 14553-14558. (Sep. 5, 2007).
Sniadecki et al., "Magnetic Microposts for Mechanical Stimulation of Biological Cells: Fabrication, Characterization, and Analysis." Rev. Sci. Instrum., vol. 79, No. 4 (Jan. 1, 2008).
Solomon et al.. Platelet function following trauma. A multiple electrode aggregometry study. Thromb Haemost 106, 322-330, (2011).
Sorensen et al. (2012). Emerging treatment strategies for trauma-induced coagulopathy. Br J Surg 99 Suppl 1: 40-50.
Spalding et al. (2007). Cost reduction of perioperative coagulation management in cardiac surgery: value of "bedside" thrombelastography (ROTEM). Eur J Cardiothorac Surg 31(6): 1052-1057.
Strony et al. (1993) Analysis of shear stress and hemodynamic factors in a model of coronary artery stenosis and thrombosis. Am J Physiol 265(5 Pt 2):H1787-1796.
Szanto et al. (2012) New insights into von Willebrand disease and platelet function. Seminars in thrombosis and hemostasis 38(1):55-63.
Tambe et al. Collective cell guidance by cooperative intercellular forces. Nature Materials 10: 469-475, 2011.
Tan et al. (2003) Cells lying on a bed of microneedles: an approach to isolate mechanical force. Proc Natl Acad Sci U S A. 100(4): p. 1484-9.
Tan et al. (2004) Simple approach to micropattern cells on common culture substrates by tuning substrate wettability. Tissue Eng. 10(5-6): p. 865-72.
Ting et al. (2012). Flow mechanotransduction regulates traction forces, intercellular forces, and adherens junctions. Am J Physiol Heart Circ Physiol 302(11): H2220-2229.
Tovar-Lopez et al., A microfluidics device to monitor platelet aggregation dynamics in response to strain rate micro-gradients in flowing blood. Lab Chip, 2010. 10(3): p. 291-302.
Trepat et al. Physical forces during collective cell migration. Nat Phys 5: 426-430, 2009.
Turitto et al. (1980) Red blood cells: their dual role in thrombus formation. Science. 207(4430): p. 541-3.
Tzima E. Role of small GTPases in endothelial cytoskeletal dynamics and the shear stress response. Circ Res 98: 176-185, 2006.
Tzima et al. Activation of integrins in endothelial cells by fluid shear stress mediates Rho-dependent cytoskeletal alignment. Embo J 20: 4639-4647, 2001.
Tzima et al. Activation of Rac1 by shear stress in endothelial cells mediates both cytoskeletal reorganization and effects on gene expression. Embo J 21: 6791-6800, 2002.
Tzima et al. Localized cdc42 activation, detected using a novel assay, mediates microtubule organizing center positioning in endothelial cells in response to fluid shear stress. J Biol Chem 278: 31020-31023, 2003.
Ukropec et al. Regulation of VE-cadherin linkage to the cytoskeleton in endothelial cells exposed to fluid shear stress. Exp Cell Res 273: 240-247, 2002.
Vidreicher et al. (2007) Dynamic interaction between Src and C-terminal Src kinase in integrin alphaIIbbeta3-mediated signaling to the cytoskeleton. J Biol Chem. 282(46): p. 33623-31.
Weisel, J.W. (2007) Structure of fibrin: impact on clot stability. J Thromb Haemost. 5 Suppl 1: p. 116-24.
Weisenberg et al. (2002). Hemocompatibility of materials used in microelectromechanical systems: Platelet adhesion and morphology in vitro. Journal of Biomedical Materials Research 60(2): 283-291.
White et al. Coagulopathy and traumatic shock: characterizing hemostatic function during the critical period prior to fluid resuscitation. Resuscitation 81, 111-116, (2010).
Whitesides et al. Soft lithography in biology and biochemistry. Annu Rev Biomed Eng 3, 335-373, (2001).
Wohlauer et al. (2012). Early platelet dysfunction: an unrecognized role in the acute coagulopathy of trauma. J Am Coll Surg 214(5): 739-746.

(56) References Cited

OTHER PUBLICATIONS

Wojciak-Stothard et al. Shear stress-induced endothelial cell polarization is mediated by Rho and Rac but not Cdc42 or PI 3-kinases. J Cell Biol161: 429-439, 2003.
Xia et al. (1998) Soft lithography. Angewandte Chemie-International Edition. 37(5): p. 551-575.
Yamada et al. Deconstructing the cadherin-catenin-actin complex. Cell 123: 889-901, 2005.
Yang et al. (2007) Geometric considerations of micro- to nanoscale elastomeric post arrays to study cellular traction forces. Advanced Materials. 19(20): p. 3119-3123.
Yonemura et al. alpha-Catenin as a tension transducer that induces adherens junction development. Nat Cell Biol 12: 533-542, 2010.
Yoshigi et al. Quantification of stretch-induced cytoskeletal remodeling in vascular endothelial cells by image processing. Cytometry A 55: 109-118, 2003.
Extended European Search Report dated Jun. 23, 2016 in European Application No. 16156781.3, 7 pages.
Office Action dated Jul. 5, 2016 in Chinese Application No. 201380036951.8, 8 pages.
Hahn et al. "Machanotransduction in Vascular Physiology and Atherogenesis" Nat. Rev. Mol. Cell. Biol. 10:53-62, 2009.
Holcomb et al. Admission Rapid Thrombelastography Can Replace Conventional Coagulation Tests in the Emergency Department: Experience with 1974 Consecutive Trauma Patients. Ann. Surg. 256(3), pp. 476-486.
Examination Report dated Oct. 31, 2016 in Canadian Patent Application No. 2,915,866, 4 pages.
Extended EP Search Report dated Nov. 17, 2016 for EP14817669.6 filed Jun. 26, 2014, 10 pages.
International Search Report and Written Opinion dated Oct. 22, 2014 in PCT/US2014/044448, 15 pp.
U.S. Appl. No. 61/391,340, filed Oct. 8, 2010.
International Application No. PCT/US2013/031782, filed Mar. 14, 2013.
Liang et al. "Platelet Retraction Force Measurements Using Flexible Post Force Sensors," Lab Chip, vol. 10, No. 8 (Jan. 1, 2010) pp. 991-997.
Sniadecki et al. "Magnetic Microposts for Mechanical Stimulation of Biological Cells: Fabrication, Characterization, and Analysis," Review of Scientific Instruments, vol. 79, No. 4 (Apr. 16, 2008) pp. 44302-1-44302-7.
U.S. Appl. No. 13/663,339, filed Oct. 29, 2012.
U.S. Appl. No. 61/645,191, filed May 10, 2012.
U.S. Appl. No. 61/709,809, filed Oct. 4, 2012.
U.S. Appl. No. 61/760,849, filed Feb. 5, 2013.
Konstantoulaki, M. et al., "Protein kinase C modifications of VE-cadherin, p120, and beta-catenin contribute to endothelial barrier dysregulation induced by thrombin", American Journal of Physiology Lung Cellular and Molecular Physiology, 285(2):L434-L442, Aug. 2003.
Lam, RHW et al., "Elastomeric microposts integrated into microfluidics for flow-mediated endothelial mechanotransduction analysis", Lab on a Chip, 12(10):1865-1873, Feb. 2012.
Alevriadou et al. (1993) Real-time analysis of shear-dependent thrombus formation and its blockade by inhibitors of von Willebrand factor binding to platelets. Blood 81(5):1263-1276.
Alon et al. (2007) Force as a facilitator of integrin conformational changes during leukocyte arrest on blood vessels and antigen-presenting cells. Immunity. 26(1): p. 17-27.
Anand et al. (2006) A viscoelastic fluid model for describing the mechanics of a coarse ligated plasma clot Theoretical and Computational Fluid Dynamics. 20(4): p. 239-250.
Arias-Salgado et al. (2008) Variations in platelet protein associated with arterial thrombosis. Thromb Res. 122(5): p. 640-7.
Back et al. (1977) Analysis of pulsatile, viscous blood flow through diseased coronary arteries of man. J Biomech 10(5-6):339-353.
Barg et al. (2007) Soluble plasma-derived von Willebrand factor assembles to a haemostatically active filamentous network. Thromb Haemost 97(4):514-526.

Baselt et al. (1998). A biosensor based on magnetoresistance technology. Biosensors & Bioelectronics 13(7-8): 731-739.
Basmadjian, D. (1984) The hemodynamic forces acting on thrombi, from incipient attachment of single cells to maturity and embolization. J Biomech. 17(4): p. 287-98.
Basmadjian, D. (1986) The hemodynamic and embolizing forces acting on thrombi—II. The effect of pulsatile blood flow. J Biomech. 19(10): p. 837-45.
Basmadjian, D. (1989) Embolization: critical thrombus height, shear rates, and pulsatility. Patency of blood vessels. Journal of Biomedical Materials Research. 23(11 ): p. 1315-26.
Brass et al. (2005) Minding the gaps to promote thrombus growth and stability. J Clin Invest. 115(12): p. 3385-92.
Brohi et al. (2008). Acute coagulopathy of trauma: hypoperfusion induces systemic anticoagulation and hyperfibrinolysis. J Trauma 64(5): 1211-1217; discussion 1217.
Brohi et al. Acute traumatic coagulopathy. J Trauma 54, 1127-1130, (2003).
Calaminus et al. (2007) MyosinIIa contractility is required for maintenance of platelet structure during spreading on collagen and contributes to thrombus stability. J Thromb Haemost. 5(10): p. 2136-45.
Carr et al. (1991) Measurement of platelet-mediated force development during plasma clot formation. Am J Med Sci. 302(1): p. 13-8.
Carr et al. (2002) Enhanced platelet force development despite drug-induced inhibition of platelet aggregation in patients with thromboangiitis obliterans—two case reports. Vase Endovascular Surg. 36(6): p. 473-80.
Carr, M.E. (2004) Monitoring Hemostasis in Combat Trauma Patients. Military Medicine. 169(12): p. 11-15.
Carr, M.E., Jr. (2003) Development of platelet contractile force as a research and clinical measure of platelet function. Cell Biochem Biophys. 38(1 ): p. 55-78.
Carroll et al. (2009) Early evaluation of acute traumatic coagulopathy by thrombelastography. Transl Res. 154(1): p. 34-9.
Chien S. Effects of disturbed flow on endothelial cells. Ann Biomed Eng 36: 554-562, 2008.
Chiu et al. Effects of disturbed flow on endothelial cells. J Biomech Eng 120: 2-8, 1998.
Chu et al. Force measurements in E-cadherin-mediated cell doublets reveal rapid adhesion strengthened by actin cytoskeleton remodeling through Rae and Cdc42. J Cell Biol 167: 1183-1194, 2004.
Cohen et al. (1973) Platelet contractile regulation in an isometric system. Nature. 246(5427): p. 36-7.
Cohen et al. (1982) Ultrastructure of clots during isometric contraction. J Cell Biol. 93(3): p. 775-87.
Cohen et al. (1989) The effect of peptides and monoclonal antibodies that bind to platelet glycoprotein IIb-IIIa complex on the development of clot tension. Blood. 73(7): p. 1880-7.
Counts et al. (1979) Hemostasis in massively transfused trauma patients. Ann Surg. 190(1): p. 91-9.
Dai et al. Distinct endothelial phenotypes evoked by arterial waveforms derived from atherosclerosis-susceptible and -resistant regions of human vasculature. Proc Natl Acad Sci US A 101: 14871-14876, 2004.
Dasta et al. (2005). Daily cost of an intensive care unit day: the contribution of mechanical ventilation. Critical Care Medicine 33(6): 1266-1271.
Davies PF. Flow-mediated endothelial mechanotransduction. Physiological Reviews 75: 519-560, 1995.
Dayananda et al. (2010) von Willebrand factor self-association on platelet GpIbalpha under hydrodynamic shear: effect on shear-induced platelet activation. Blood 116(19):3990-3998.
Dejana E. Endothelial cell-cell junctions: happy together. Nat Rev Mol Cell Biol 5: 261-270, 2004.
Desai et al. (2007) Microfabricated Post•Array-Detectors (mPADs): An Approach to Isolate Mechanical Force. Journal of Visualized Experiments. (7) p. 1-4.
Doggett et al. (2002) Selectin-like kinetics and biomechanics promote rapid platelet adhesion in flow: the GPib(alpha)-vWF tether bond. Biophys J 83(1):194-205.

(56) References Cited

OTHER PUBLICATIONS

Dopheide, et al. Shear-dependent tether formation during platelet translocation on von Willebrand factor. Blood, 2002. 99(1): p. 159-67.

Dudek et al. Cytoskeletal regulation of pulmonary vascular permeability. J Appl Physiol 91: 1487-1500, 2001.

Duffy et al. (1998) Rapid prototyping of microfluidic systems in poly(dimethylsiloxane). Analytical Chemistry. 70(23): p. 4974-4984.

Ethier et al. Introductory biomechanics from cells to organisms. 2007, Cambridge University Press: Cambridge; New York. p. xiii, 511 p., [16] p. of plates.

Fabian et al. An enhancer of myosin, speeds up anaphase chromosome movement. Cell Chromosome 6: 1, 2007.

Feghhi et al. (2011). Mechanobiology of Platelets: Techniques to Study the Role of Fluid Flow and Platelet Retraction Forces at the Micro- and Nano-Scale. International Journal of Molecular Sciences 12(12): 9009-9030.

Feng et al. (2006) Pathological shear stress directly regulates platelet alphaIIbbeta3 signaling. Am J Physiol Cell Physiol 291(6):C1346-1354.

Freitas et al. (2007). Magnetoresistive sensors. Journal of Physics—Condensed Matter 19(16).

Frith et al. (2012). Acute traumatic coagulopathy. Current Opinion in Anesthesiology 25(2): 229-234.

Furie, et al. (2008) Mechanisms of thrombus formation. N Engl J Med. 359(9): p. 938-49.

Ganter et al. (2008). Coagulation monitoring: current techniques and clinical use of viscoelastic point-of-care coagulation devices. Anesth Analg 106(5): 1366-1375.

Geiger et al. (2001) Transmembrane extracellular matrix•cytoskeleton crosstalk. Nat Rev Mol Cell Biol. 2(11 ): p. 793-805.

Gimbrone MA. The Gordon Wilson lecture: Understanding vascular endothelium: a pilgrim's progress: endothelial dysfunction, biomechanical forces and the pathobiology of atherosclerosis. Trans Am Clin Climatol Assoc 121: 115-127; discussion 127, 2010.

Gomez-Sjoberg et al. (2007) Versatile, fully automated, microfluidic cell culture system. Anal Chem. 79(22): p. 8557-63.

Greilich et al. (1995) Reductions in platelet force development by cardiopulmonary bypass are associated with hemorrhage. Anesth Analg. 80(3): p. 459-65.

Griffiths et al. (2001) Low dispersion turns and junctions for microchannel systems. Analytical Chemistry. 73(2): p. 272-278.

Grunkemeier et al. (2000) The effect of adsorbed fibrinogen, fibronectin, von Willebrand factor and vitronectin on the procoagulant state of adherent platelets. Biomaterials. 21(22): p. 2243-52.

Office Action dated Feb. 7, 2017 in Japan Application No. 2015-511464, 11 pages.

Examiner's Report dated Sep. 5, 2017 in Canadian Patent Application No. 2,915,866, 3 pages.

First Examination Report in Australian Patent Application No. 2013260125, dated Nov. 24, 2017, 5 pages.

Non-Final Office Action in U.S. Appl. No. 14/902,547, dated Oct. 20, 2017 of Sniadecki, N. et al, filed Dec. 31, 2015.

Non-Final Office Action dated Oct. 25, 2017 in U.S. Appl. No. 14/934,540, of Sniadecki, N. et al., filed Nov. 6, 2015.

Raymond et al, "Elastomeric microposts integrated into microfluidics for flow-mediated endothelial mechanotransduction analysis", Lab on a Chip: Miniaturization for chemistry, physics, biology, materials science and bioengineering, vol. 12;10; 1865, Feb. 28, 2012.

Extended European Search Report dated Jun. 23, 2016 in European Patent Application No. 16156781.3, 7 pages.

Final Office Action dated Jun. 11, 2015 in U.S. Appl. No. 14/126,412, of Sniadecki, N. et al., filed Dec. 13, 2013.

Final Office Action dated Aug. 25, 2014 in U.S. Appl. No. 13/663,339, of Sniadecki, N. et al., filed Oct. 29, 2012.

Non-Final Office Action dated Feb. 3, 2015 in U.S. Appl. No. 14/126,412, of Sniadecki, N. et al., filed Dec. 13, 2013.

Non-Final Office Action dated Mar. 17, 2014 in U.S. Appl. No. 13/663,339 of Sniadecki, N. et al., filed Oct. 29, 2012.

Notice of Allowance dated Oct. 30, 2014 in U.S. Appl. No. 13/663,339 of Sniadecki, N. et al., filed Oct. 29, 2012.

Notice of Allowance dated Jun. 18, 2015 in U.S. Appl. No. 13/663,339 of Sniadecki, N. et al., filed Oct. 29, 2012.

Notice of Allowance dated Aug. 26, 2015 in U.S. Appl. No. 14/126,412 of Sniadecki, N. et al., filed Dec. 13, 2013.

Final Office Action dated Apr. 3, 2018 in U.S. Appl. No. 14/934,540 of Sniadecki, N. et al., filed Nov. 6, 2015.

First Examination Report in Australian Patent Application No. 2014302312, dated Apr. 19, 2018, 3 pages.

Final Office Action dated May 4, 2018 in U.S. Appl. No. 14/902,547, for Sniadecki, N. et al., filed Dec. 31, 2015.

\* cited by examiner

Fig. 5 ns of orientatiDEVICES TO EXPOSE CELLS TO FLUID
SHEAR FORCES AND ASSOCIATED
SYSTEMS AND METHODS

CROSS-REFERENCE TO RELATED APPLICATION

This application is a divisional of U.S. application Ser. No. 13/663,339, filed Oct. 29, 2012, which claims benefit of U.S. Provisional Patent Application No. 61/552,052, filed Oct. 27, 2011; U.S. Provisional Patent Application No. 61/645,191, filed May 10, 2012; and U.S. Provisional Patent Application No. 61/709,809, filed Oct. 4, 2012, each of which is incorporated herein by reference in its entirety.

STATEMENT REGARDING FEDERALLY-SPONSORED RESEARCH

This invention was made with government support under 5T32EB001650 and 5R21HL097284 awarded by the National Institutes of Health, and N66001-11-1-4129 awarded by the Space and Naval Warfare Systems Center (SPAWAR). The government has certain rights in the invention.

TECHNICAL FIELD

The present technology relates generally to devices to expose cells to fluid shear forces and associated systems and methods. In particular, several embodiments are directed toward devices to expose cells to fluid shear forces in order measure changes in internal cell forces.

BACKGROUND

Mechanical forces are important modulators of cellular function in many tissues. For example, mechanotransduction responses to laminar or disturbed flow can strongly affect the ability of endothelial cells to maintain the barrier between blood and the vessel wall. Laminar flow occurs in straight vessels and produces a steady shear stress on the cells. Disturbed flow forms downstream of obstructions, bends, or bifurcations, and produces a time-averaged, low shear stress due to eddies in the flow. These flows can activate mechanosensors in endothelial cells that lead to the activation of signaling pathways that affect cytoskeletal structures. In particular, laminar flow can initiate Rho GTPase pathways that cause alignment of actin filaments and assembly of adherens junctions. Conversely, disturbed flow leads to disorganized actin, disassembly of adherens junctions, and small gaps between adjacent endothelial cells. These structural changes in endothelial cells can strongly affect the integrity of the vascular barrier.

DETAILED DESCRIPTION

The present technology relates generally to devices to expose cells to fluid shear forces and associated systems and methods. In particular, several embodiments are directed toward devices to expose cells to fluid shear forces in order to measure changes in internal cell forces. In some embodiments, a fluidic device includes a flow unit configured to induce fluid flow through the device. The device further includes a fluid channel configured to accept a biological sample dispersed on an array of flexible structures. The flow unit can be configured to induce disturbed and laminar flow in the fluid channel. The device can further include detection means configured to measure a degree of deflection of one or more flexible structures in the array.

Specific details of several embodiments of the technology are described below with reference to FIGS. 1-5. Other details describing well-known structures and systems often associated with cellular research tools have not been set forth in the following disclosure to avoid unnecessarily obscuring the description of the various embodiments of the technology. Many of the details, dimensions, angles, and other features shown in the Figures are merely illustrative of particular embodiments of the technology. Accordingly, other embodiments can have other details, dimensions, angles, and features without departing from the spirit or scope of the present technology. A person of ordinary skill in the art, therefore, will accordingly understand that the technology may have other embodiments with additional elements, or the technology may have other embodiments without several of the features shown and described below with reference to FIGS. 1-5.

Figure 1A:
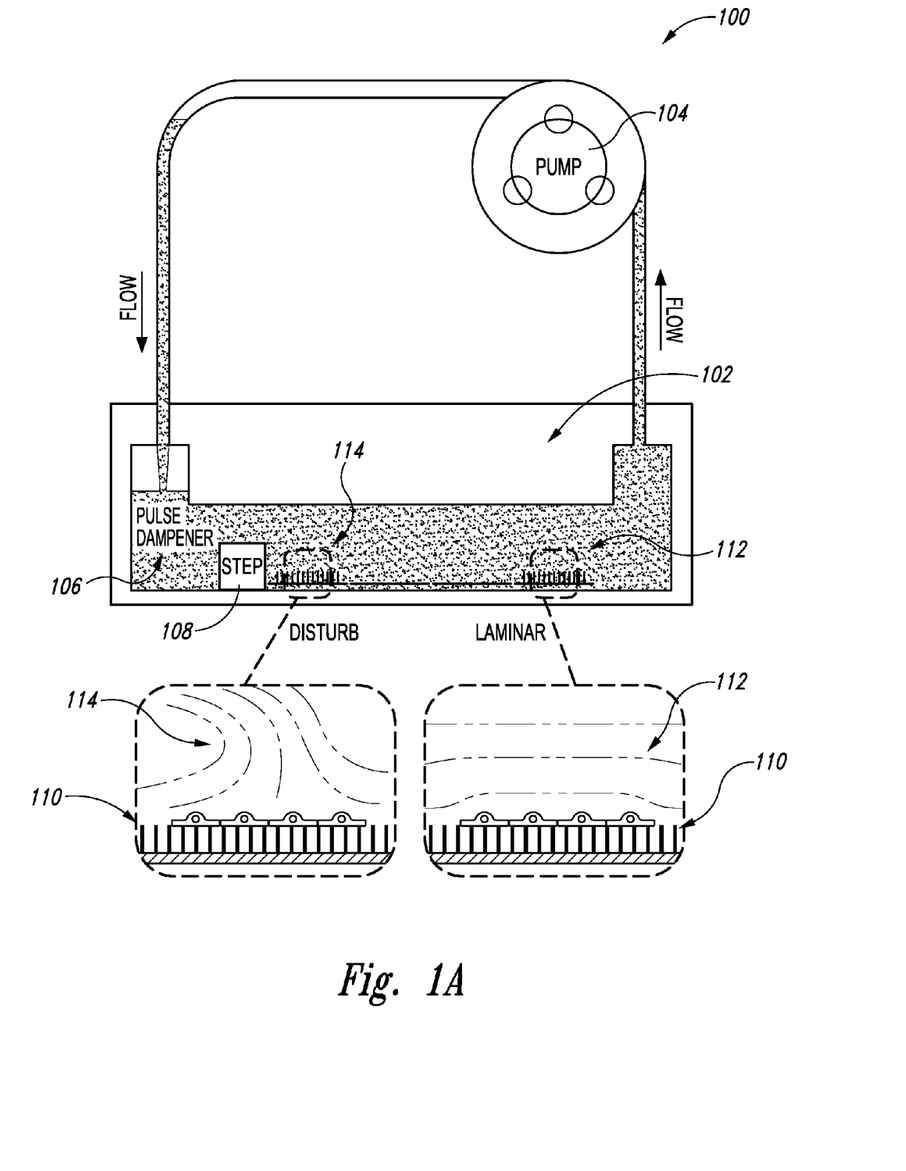
FIG. 1A is a partially schematic illustration of a cellular flow chamber configured in accordance with embodiments of the technology.

FIG. 1A is a partially schematic illustration of a parallel plate fluid flow chamber 100 configured in accordance with embodiments of the technology. In several embodiments, the flow chamber 100 is sized for benchtop use to simulate fluid shear stresses on various cell types exposed to laminar and dynamic fluid flow in their natural, physiological environment. In some embodiments, at least a portion of the flow chamber 100 is constructed of clear acrylic or other suitable material.

The chamber 100 can include a main channel 102 through which pumped fluid flows. In one embodiment, the main channel 102 has a length of 100 mm, a width of 20 mm, and a depth of 0.5 mm. The main channel 102 can have other dimensions in other embodiments. While FIG. 1A illustrates a single main channel 102, in further embodiments the chamber 100 can include a plurality of fluid channels. The main channel 102 is configured to accept one or more individual or arrays 110 of microposts. As discussed in further detail below with reference to FIG. 1B, in some embodiments, the array 110 comprises a biological sample that is cultured as monolayers on micropost substrates. In several embodiments, the sample comprises human pulmonary artery endothelial cells, or HPAECs. In further embodiments, the sample comprises whole blood, platelets, tumor cells, protein solutions, fibroblasts, smooth muscle cells, cardiomyocytes, white blood cells, red blood cells, or fragments thereof. The sample may comprise other types of biological material in still further embodiments. In embodiments with multiple fluid channels, a user can introduce different fluids, biological samples, and/or reagents in the different channels.

Figure 1B:
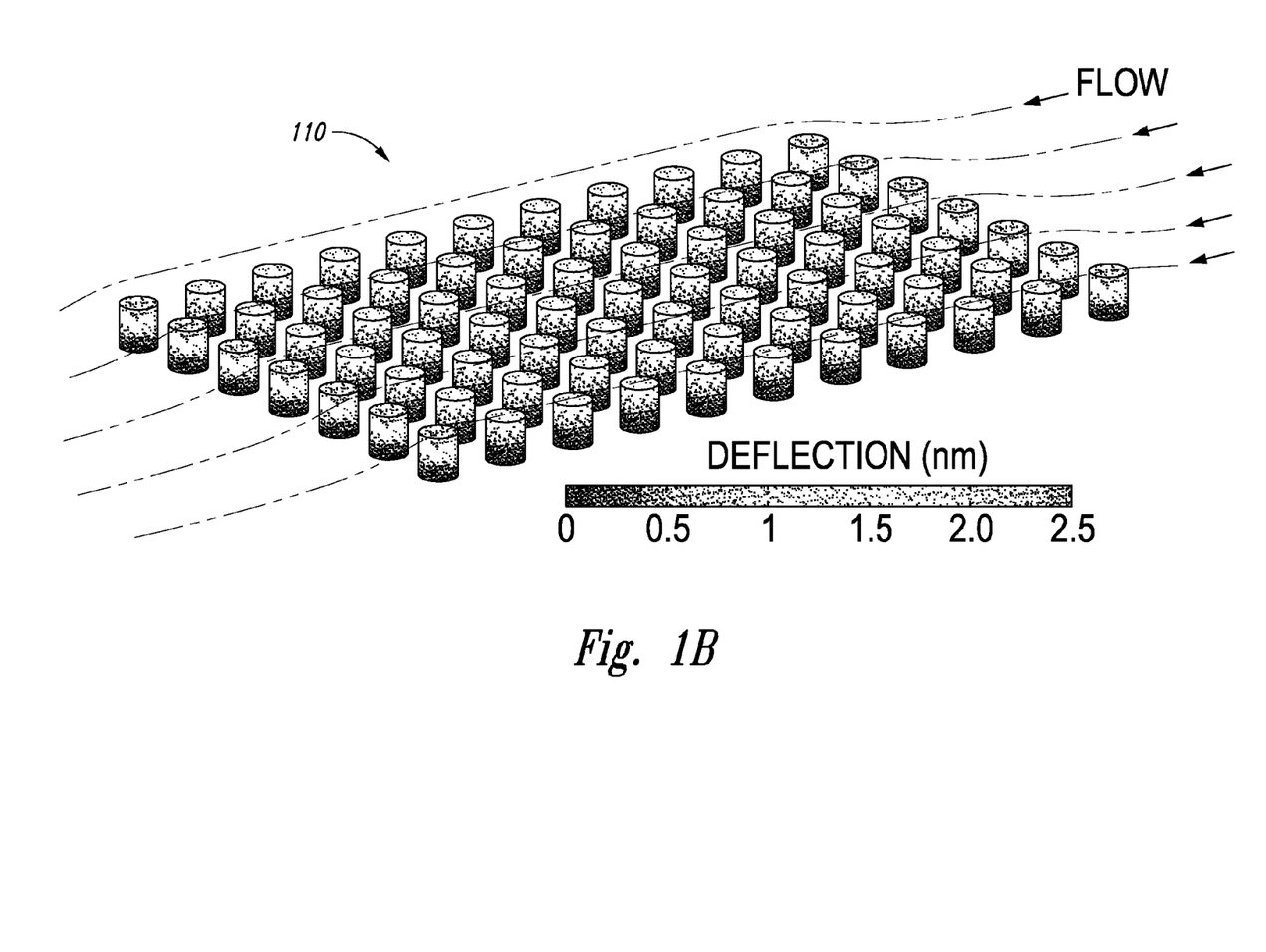
FIG. 1B is an isometric, partially schematic illustration of an array of micropost substrates configured for placement in the cellular flow chamber of FIG. 1A in accordance with embodiments of the technology.

FIG. 1B is an isometric, partially schematic illustration of the array 110 of micropost substrates configured for placement in the fluid flow chamber 100 of FIG. 1A in accordance with embodiments of the technology. In some embodiments, the array 110 is created by casting a film of polydimethylsiloxane (PDMS) or similar material with a 0.25 mm thickness on a No. 2 glass coverslip. In other embodiments, other materials and/or thicknesses of materials can be used. In some embodiments, the individual microposts comprise silicon, polymers, metal, or ceramics. In some embodiments, the microposts or other portion of the chamber 100 is substantially coated in a non-fouling coating. In a particular embodiment, individual microposts have a diameter from about 1 nm to about 50 µm and/or an aspect ratio between about 1:1 and about 1:100. In further embodiments, the microposts can have other dimensions.

The arrays 110 of microposts can be micromolded into a desired arrangement. In order to prepare either flat substrates or microposts for cell attachment, a binding element (e.g., fibronectin) can be absorbed onto the surface of a PDMS stamp. The stamps can have no pattern ("flat stamp") or an array of positive relief patterns in the shape of a grid of squares ("square stamps"). Once the protein is adsorbed, the stamp can be placed into conformal contact with the substrate in order to transfer fibronectin onto the regions of contact. Afterwards, each substrate can be treated with 0.2% Pluronic F127 or other suitable material to ensure that cells adhere to regions where the fibronectin was printed.

As discussed above, in some embodiments, the substrates support HPAECs, which are seeded at confluent densities onto arrays of microposts or flat substrates. In some embodiments, the individual microposts are substantially coated with at least one binding element, such as proteins, glycans, polyglycans, glycoproteins, fibrinogen, fibronectin, von Willebrand Factor, collagen, vitronectin, laminin, monoclonal antibodies, polyclonal antibodies, and/or fragments thereof. Cells can be allowed to spread and reform their adherens junctions for a selected time period (e.g., two days) in culture before subjecting them to flow conditions. Microposts can act as elastic, cantilever beams which deflect in proportion to the force applied at their tips. Representative deflection caused by the Flow F applied to the array 110 is illustrated in FIG. 1B as a continuum from micropost base to tip.

Referring to FIGS. 1A and 1B together, in operation, the micropost arrays 110 are placed in the main channel 102 and exposed to static, laminar, and/or disturbed flow conditions for a selected time period. For example, in some embodiments, the substrate arrays 110 with HPAEC monolayers can be placed inside the chamber 100 and shear force can be applied for the selected time period. In one embodiment, the shear force is applied continuously for 14 hours. In other embodiments, the force is applied intermittently or for more or less than 14 hours.

A flow rate (e.g., a steady flow rate of 2 mL) can be produced by a flow unit (e.g., a pump) 104 that is connected to the flow chamber 100 and configured to recirculate the media through the chamber 100 in the direction of the flow arrows. In a particular embodiment, the flow unit 104 is capable of introducing the shear stress from about −10 kPa to about 10 kPa. The flow unit 104 can comprise a positive displacement pump, a piezoelectric pump, a partial vacuum, a diaphragm pump, a peristaltic pump, a hydrostatic pump, or another device. The fluid passing through the chamber 100 can be any type of fluid configured to induce the desired shear stress on the array 110. In some embodiments, the fluid contains a drug, reagent, nucleotide, protein, or a material that can cause the cells bound to the microposts to contract.

A chamber of air 106 at the entrance of the channel 102 can damp the pulsatile flow so that a steady flow rate is produced in the channel 102. The air chamber 106 can be either upstream or downstream of the array 110. A backward-facing step 108 in the channel 102 can produce a region of disturbed flow 114 downstream from the step 108. In a particular embodiment, the step 108 is 0.25 mm tall. Flow in the disturbed flow region 114 can have separation in its fluid stream lines, stagnation points, and regions of reversal in the direction of flow. A laminar flow region 112 can occur further downstream from the region of disturbed flow 114. In further embodiments, the disturbed flow region 114 and laminar flow region 112 can be in other positions relative to one another or relative to the main channel 102. In still further embodiments, only one of disturbed flow or laminar flow is produced.

Changes in traction forces, intercellular forces, and adherens junctions can be measured to understand the role of tension at the cell-cell interface in regulating the endothelial barrier. For example, the degree of effect from the flow can be optically determined More specifically, to measure the deflection of a micropost, the difference between the position of its tip and base can be analyzed from fluorescent images taken at the top and bottom of the arrays 110. The magnitude and direction of each traction force (F) can be computed from the deflection (δ) through the relationship:

$$F = \frac{3\pi E D^4}{64 L^3} \delta$$

The length L and diameter D of the microposts in the array can be measured using a scanning electron microscope. Young's modulus of PDMS (E=2.5 MPa) can be determined by tensile testing. Cytoskeletal tension can be assessed by computing the average traction force per monolayer. Intercellular forces can be determined by the vector sum of the traction forces on a cell in a monolayer. Intercellular tension can be measured by the average intercellular force for cells within a monolayer.

In further embodiments, deflection can be determined by magnetic detection means. For example, magnetic nanowires can be embedded into microposts to apply external forces to cells. In some embodiments, the nanowires comprise cobalt or nickel wires grown by electrochemical deposition in the pores of a template. The magnetic microposts can be actuated by applying a uniform field (e.g., in a direction perpendicular to the long axis of the posts). The induced magnetic torque on the nanowire causes the magnetic posts to deflect; the field thereby applies nanonewtons of force to the biological sample. The nanowires can become rotated by the deflection of the posts. Micropost deflection can be detected using a Hall probe placed adjacent to (e.g., underneath) the magnetized array 110.

Figure 2A:
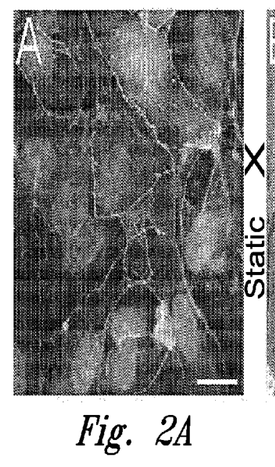
FIGS. 2A-2C are illustrations of cells cultured on flat substrates and placed under static, laminar, or disturbed flow conditions and configured in accordance with embodiments of the technology.
Figure 2B:
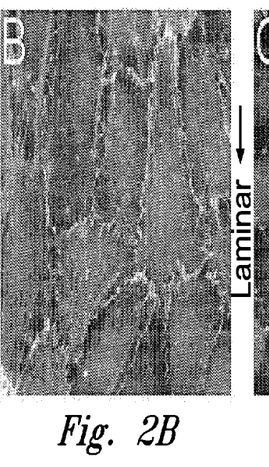
Figure 2C:
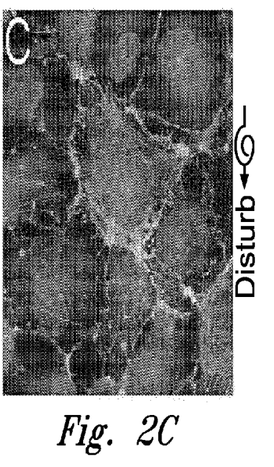
Figure 2D:
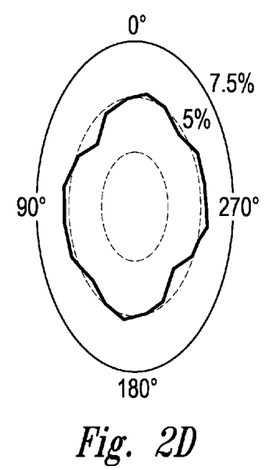
FIGS. 2D-2F are rose plots illustrating the orientations of the cells of FIGS. 2A-2C, respectively, in accordance with embodiments of the present technology.
Figure 2E:
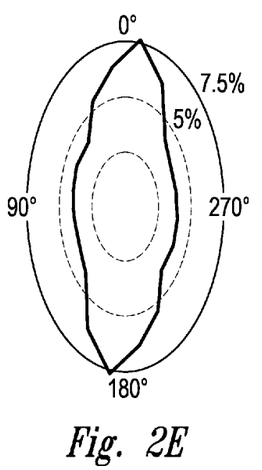
Figure 2F:
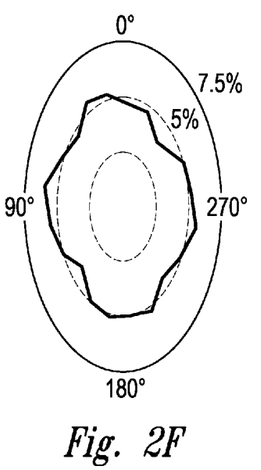

FIGS. 2A-2C are representative immunofluorescent images of HPAECs cultured on flat substrates and placed under (A) static, (B) laminar, or (C) disturbed flow conditions for a selected time period (e.g., 14 hours). FIGS. 2D-2F are rose plots illustrating the orientations of the HPAECs of FIGS. 2A-2C, respectively. Endothelial cells can align their actin filaments in the direction of shear flow on flat substrates. HPAECs grown on flat substrates can align their actin filaments parallel to the direction of laminar flow, whereas under static and disturbed flow, their actin may have no preferential alignment.

Figure 3A:
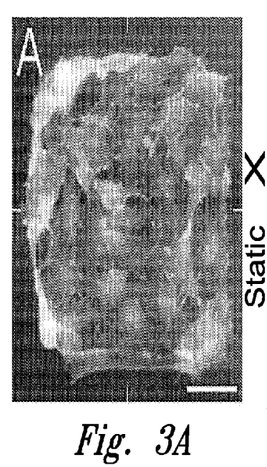
FIGS. 3A-3C are illustrations of cells cultured on microposts and placed under static, laminar, or disturbed flow conditions and configured in accordance with embodiments of the technology.
Figure 3B:
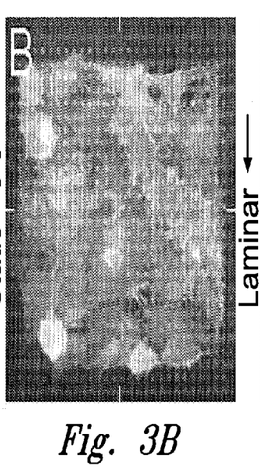
Figure 3C:
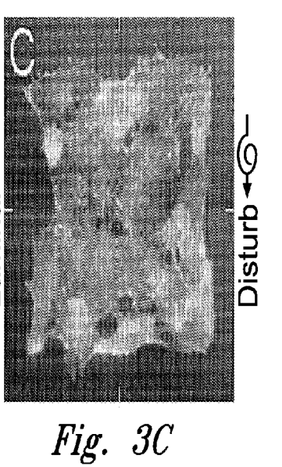
Figure 3D:
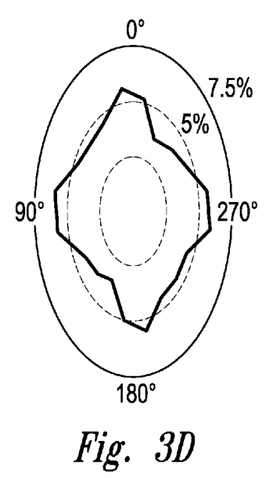
FIGS. 3D-3F are rose plots illustrating the orientations of the cells of FIGS. 3A-3C, respectively, in accordance with embodiments of the present technology.
Figure 3E:
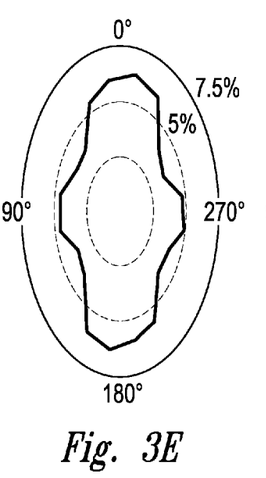
Figure 3F:
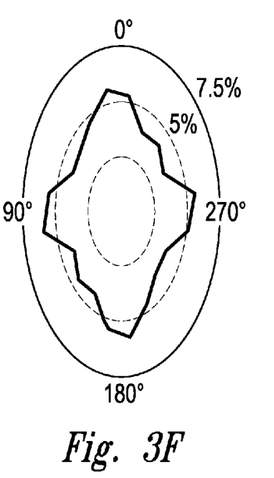

FIGS. 3A-3C are representative illustrations of HPAECs cultured on microposts and placed under static, laminar, or disturbed flow conditions and configured in accordance with embodiments of the technology. FIGS. 3D-3F are rose plots illustrating the orientations of HPAECs of FIGS. 3A-3C, respectively. Similar to the cells described above with reference to FIGS. 2A-2F, actin filaments are oriented predominately in the direction of laminar flow. This does not hold true for static or disturbed flow. There is, however, a strong degree of actin alignment along the 0°, 90°, 180°, and 270° directions for all flow conditions, which can match the orthogonal arrangement of the microposts in the sample array (e.g., the array 110 illustrated in FIG. 1B). These alignment results are due to focal adhesions that can form at the microposts and therefore help to confine actin filaments between adjacent posts. However, laminar flow can create a stronger degree of alignment of actin in the direction of flow despite the strong influence of the arrangement of the microposts.

Figure 4A:
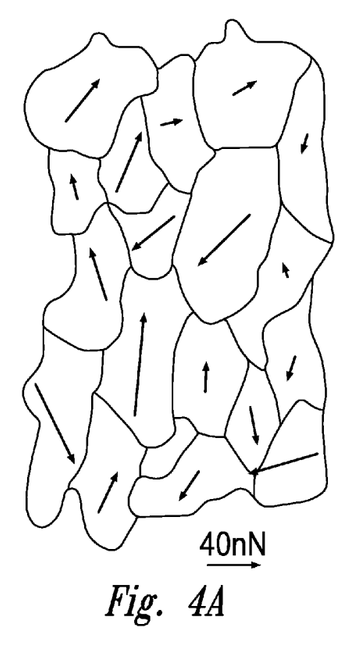
FIG. 4A is an illustration of vector fields of intercellular force in accordance with embodiments of the technology.
Figure 4B:
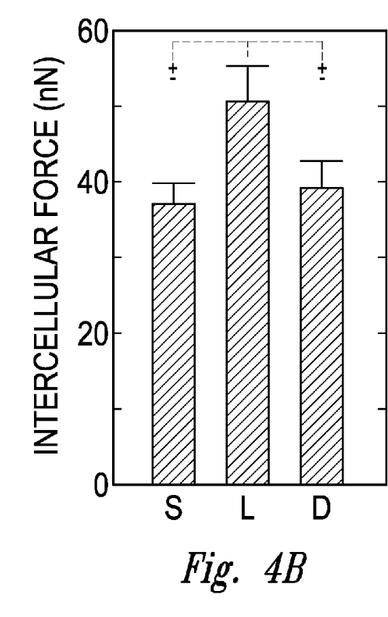
FIG. 4B is a graph illustrating intercellular forces under static, laminar, and disturbed flow conditions in accordance with embodiments of the technology.

FIG. 4A is an illustration of vector fields of intercellular force for a representative HPAEC monolayer exposed to shear force for a selected time period (e.g., 14 hours) in accordance with embodiments of the technology. FIG. 4B is a graph illustrating representative intercellular forces calculated by the vector sum of the tugging forces acting on a cell under static (S), laminar (L), and disturbed (D) flow in accordance with embodiments of the technology. Referring to FIGS. 4A and 4B together, a shear force testing device (such as the fluid flow device) can provide significant information regarding intercellular force. For example, vector fields of intercellular force illustrate that cells with large intercellular forces acting on them are located not only at the perimeter, but within the interior of the monolayer as well. Cytoskeletal tension can be transmitted as traction forces at the microposts, but also as intercellular forces between adjacent cells within a monolayer. The average intercellular force may be higher for laminar flow as compared to static and disturbed flow conditions. Intercellular forces can increase under laminar flow and promote adherens junction assembly.

Figure 5:
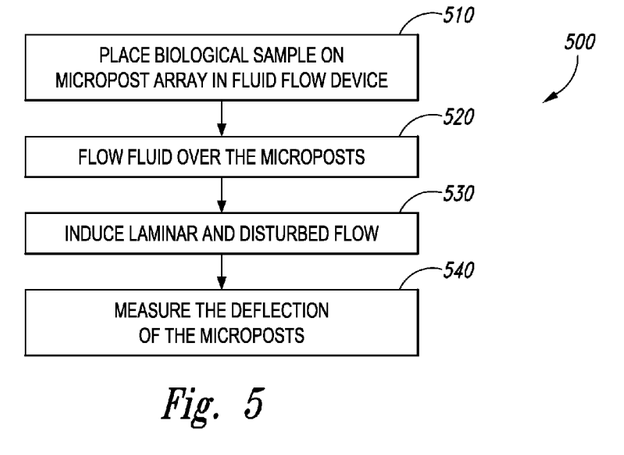
FIG. 5 is a block diagram illustrating a method of applying shear force to a biological sample in accordance with embodiments of the technology.

FIG. 5 is a block diagram illustrating a method 500 of applying shear force to a biological sample in accordance with embodiments of the technology. In some embodiments, the method 500 includes placing microposts in a fluid flow device, 510. As discussed above, the microposts can have a biological sample bound thereto. In particular embodiments, the biological sample comprises HPAECs.

The method 500 further includes flowing fluid over the microposts 520. The fluid can be induced in movement by a pump or other device. This method of flowing fluid can be accomplished in a fluid flow chamber such as the chamber described above with reference to FIG. 1A. In several embodiments, flowing fluid over the microposts comprises inducing laminar and disturbed flow conditions. In some embodiments, these flow conditions can be induced by flowing the fluid over a backward-facing step in the fluid flow chamber, wherein the laminar and disturbed flow occur downstream of the step. In further embodiments, the method can include placing an air chamber in the fluid flow chamber to induce a steady flow rate. The method 500 can further include measuring the deflection of the microposts, 540.

The technology disclosed herein offers several advantages over existing systems. For example, by using the approach of inducing shear flow over a micropost array, a quantitative image analysis can be performed to demonstrate that mechanotransduction of flow directly affects the interceullar tension in a monolayer, which coincides with the assembly of cell-cell contacts between adjacent cells. The systems disclosed herein can be used as a research tool to investigate numerous aspects of ceullar structure and behavior in various environmental conditions. For example, the systems can be used to demonstrate that laminar flow can cause a rise in cytoskeletal tension that increases traction forces and intercellular forces and promotes the assembly of adherens junctions. Disturbed flow can be found to weaken ceullar forces and cause adherens junction disassembly.

From the foregoing it will be appreciated that, although specific embodiments of the technology have been described herein for purposes of illustration, various modifications may be made without deviating from the spirit and scope of the technology. Further, certain aspects of the new technology described in the context of particular embodiments may be combined or eliminated in other embodiments. Moreover, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

We claim:

1. A fluidics device, comprising:
   a flow unit configured to induce fluid flow through the device;
   at least one fluid channel including an array of flexible structures, wherein the fluid channel is configured to accept a biological sample that includes a plurality of cells, and wherein the flexible structures are arranged within the fluid channel such that, when the biological sample is received by the fluid channel, at least some of the plurality of cells are dispersed over at least two of the flexible structures, and further wherein the fluid channel is configured to induce disturbed and laminar flow in the fluid channel; and
   a detector configured to measure a degree of deflection of one or more flexible structures in the array.

2. The device of claim 1, further comprising at least one of an air chamber or a step positioned in the fluid channel and configured to control a characteristic of fluid flow through the array.

3. The device of claim 1 wherein the biological sample comprises protein solutions, tissues, cells, or fragments of tissues or cells.

4. The device of claim 1 wherein the biological sample comprises at least one of whole blood, platelets, endothelial cells, tumor cells, fibroblasts, smooth muscle cells, cardiomyocytes, white blood cells, red blood cells, or fragments thereof.

5. The device of claim 1 wherein the flexible structures comprise microposts made of silicon, polymers, metal, or ceramics.

6. The device of claim 1 wherein individual flexible structures have a diameter from about 1 nm to about 50 μm.

7. The device of claim 1 wherein individual flexible structures have an aspect ratio between about 1:1 and about 1:100.

8. The device of claim 1 wherein the flow unit is capable of introducing shear stress to the biological sample.

9. The device of claim 8 wherein the flow unit is capable of introducing the shear stress from about −10 kPa to about 10 kPa.

10. The device of claim 1 wherein the flow unit comprises a positive displacement pump, a piezoelectric pump, a partial vacuum, a diaphragm pump, a hydrostatic pump, or a peristaltic pump.

11. The device of claim 1 wherein individual flexible structures are substantially coated in a non-fouling coating.

12. The device of claim 1 where at least one of the flow unit or the fluid chamber is substantially coated in a non-fouling coating.

13. The device of claim 1 wherein the detector comprises at least one of an optical detector or a magnetic detector.

14. The device of claim 1 wherein individual flexible structures are substantially coated with at least one binding element.

15. The device of claim 14 wherein the binding element is selected from group consisting of proteins, glycans, polyglycans, glycoproteins, fibrinogen, fibronectin, von Willebrand Factor, collagen, vitronectin, laminin, monoclonal antibodies, polyclonal antibodies, and fragments thereof.

* * * * *